US012213519B2

(12) United States Patent
Bless et al.

(10) Patent No.: US (51) Int. Cl.**
*A24F 40/10* (2020.01)
*A24F 40/485* (2020.01)
*A61M 15/00* (2006.01)
*H05B 1/02* (2006.01)
*H05B 3/26* (2006.01)

(52) U.S. Cl.
CPC ........... *H05B 1/0244* (2013.01); *H05B 3/265* (2013.01); *A24F 15/015* (2020.01); *A24F 40/10* (2020.01); *A61M 15/004* (2014.02); *H05B 2203/016* (2013.01)

(56) References Cited

U.S. PATENT DOCUMENTS

| | | |
|---|---|---|
| 2,057,353 A | 10/1936 | Whittemore, Jr. |
| 2,104,266 A | 1/1938 | McCormick |
| 3,200,819 A | 8/1965 | Gilbert |
| 3,479,561 A | 11/1969 | Janning |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 10,279,934 B2 | 5/2019 | Christensen et al. |
| 10,694,782 B2 | 6/2020 | Liu |
| 10,842,197 B2* | 11/2020 | Bless .................. H05B 1/0244 |
| 2002/0128629 A1* | 9/2002 | Antoine ................ A61J 1/2089 |
| | | 604/414 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0186738 A1 | 7/2010 | Kobayashi et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1* | 1/2011 | Xiu .......................... A24F 40/42 |
| | | 131/273 |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |

(56) References Cited

U.S. PATENT DOCUMENTS

| | | |
|---|---|---|
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0213419 A1* | 8/2013 | Tucker ............... H05B 3/34 131/328 |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0000788 A1* | 1/2015 | McAllister ............ A61M 5/329 141/329 |
| 2015/0007838 A1 | 1/2015 | Fernando et al. |
| 2015/0053217 A1 | 2/2015 | Steingraber et al. |
| 2016/0000147 A1 | 1/2016 | Li et al. |
| 2016/0037826 A1 | 2/2016 | Hearn et al. |
| 2016/0206004 A1* | 7/2016 | Shinkawa .............. B65D 85/70 |
| 2016/0286860 A1* | 10/2016 | Flayler ................. A61M 11/042 |
| 2017/0006917 A1* | 1/2017 | Alvarez ................. A24F 40/42 |
| 2017/0042251 A1 | 2/2017 | Yamada et al. |
| 2017/0055586 A1 | 3/2017 | Liu |
| 2017/0233114 A1* | 8/2017 | Christensen ............. B65B 3/14 141/2 |
| 2017/0280771 A1 | 10/2017 | Courbat et al. |
| 2018/0070641 A1 | 3/2018 | Batista et al. |
| 2020/0114095 A1 | 4/2020 | Holroyd et al. |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 203952432 U | 11/2014 |
| CN | 205597119 U | 9/2016 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2 946 679 | 11/2015 |
| GB | 2469850 | 11/2010 |
| RU | 2 614 600 C2 | 3/2017 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2015/180370 | 12/2015 |

* cited by examiner

DETACHABLE CONTAINER FOR AEROSOL DELIVERY HAVING PIERCEABLE MEMBRANE

CROSS-REFERENCE TO RELATED APPLICATION(S)

The present application is a continuation of U.S. patent application Ser. No. 15/648,181, entitled: Detachable Container for Aerosol Delivery Having Pierceable Membrane, filed on Jul. 12, 2017, the content of which is incorporated herein by reference in its entirety.

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various implementations of products and heating configurations described in the background sections of U.S. Pat. No. 5,388,594 to Counts et al. and U.S. Pat. No. 8,079,371 to Robinson et al., which are incorporated by reference.

However, it may be desirable to provide aerosol delivery devices with improved electronics such as may extend usability of the devices.

BRIEF SUMMARY

The present disclosure relates to aerosol delivery devices, methods of forming such devices, and elements of such devices. The present disclosure includes, without limitation, the following example implementations.

Some example implementations provide a cartridge coupled or coupleable with a control body to form an aerosol delivery device, the cartridge comprising a container of aerosol precursor composition; and an atomizer enclosing a reservoir configured to receive and carry aerosol precursor composition, wherein the container and the atomizer are removably coupleable with one another, and include respectively a septum and a cannula that are engaged when the container and the atomizer are coupled to enable passage of aerosol precursor composition from the container to the reservoir, and wherein the atomizer further includes a heating element controllable to activate and vaporize components of the aerosol precursor composition in the reservoir.

In some example implementations of the cartridge of the preceding or any subsequent example implementation, or any combination thereof, the cannula includes a first passageway for the passage of aerosol precursor composition, and a second passageway for passage of air into the container.

In some example implementations of the cartridge of the preceding or any subsequent example implementation, or any combination thereof, the atomizer further includes a second cannula that is also engaged with the septum when the container and the atomizer are coupled, the second cannula and the septum being engaged to enable passage of air into the container.

In some example implementations of the cartridge of the preceding or any subsequent example implementation, or any combination thereof, the atomizer further comprises a porous element in the reservoir and configured to be at least partially saturated with the aerosol precursor composition in the reservoir.

In some example implementations of the cartridge of the preceding or any subsequent example implementation, or any combination thereof, the atomizer further comprises a transport component to enable fluid communication of aerosol precursor composition from the porous element to the heating element.

In some example implementations of the cartridge of the preceding or any subsequent example implementation, or any combination thereof, the container and the atomizer are threadably coupleable with one another.

In some example implementations of the cartridge of the preceding or any subsequent example implementation, or any combination thereof, the container and the atomizer are engagable in a snap fit connection with one another.

In some example implementations of the cartridge of the preceding or any subsequent example implementation, or any combination thereof, the container and the atomizer are engagable in a pressure fit connection with one another.

Some example implementations provide a container of aerosol precursor composition, the container comprising a connector configured to removeably couple the container with an atomizer for an aerosol delivery device, the atomizer enclosing a reservoir configured to receive and carry aerosol precursor composition; and a septum that is engaged with a cannula of the atomizer when the container and the atomizer are coupled to enable passage of aerosol precursor composition from the container to the reservoir, the atomizer further including a heating element controllable to activate and vaporize components of the aerosol precursor composition in the reservoir.

In some example implementations of the container of any preceding or any subsequent example implementation, or any combination thereof, septum being engaged with the cannula includes the septum being engaged with the cannula that includes a first passageway for the passage of aerosol precursor composition, and a second passage way for passage of air into the container.

In some example implementations of the container of any preceding or any subsequent example implementation, or any combination thereof, the septum is further engaged with a second cannula of the atomizer when the container and the atomizer are coupled, the septum and the second cannula being engaged to enable passage of air into the container.

In some example implementations of the container of any preceding or any subsequent example implementation, or any combination thereof, the septum being engaged with the cannula includes the septum being engaged with the cannula to enable passage of aerosol precursor composition from the container to a porous element in the reservoir and configured to be at least partially saturated with the aerosol precursor composition in the reservoir.

In some example implementations of the container of any preceding or any subsequent example implementation, or any combination thereof, the connector is configured to threadably couple the container with the atomizer.

In some example implementations of the container of any preceding or any subsequent example implementation, or any combination thereof, the connector is configured to snap fit the container with the atomizer.

In some example implementations of the container of any preceding or any subsequent example implementation, or any combination thereof, the connector is configured to pressure fit the container with the atomizer.

Some example implementations provide an atomizer for an aerosol delivery device, the atomizer comprising a connector configured to removeably couple the atomizer with a container of aerosol precursor composition; a reservoir configured to receive and carry aerosol precursor composition; a cannula that is engaged with a septum of the container when the atomizer and the container are coupled to enable passage of aerosol precursor composition from the container to the reservoir; and a heating element controllable to activate and vaporize components of the aerosol precursor composition in the reservoir.

In some example implementations of the atomizer of any preceding or any subsequent example implementation, or any combination thereof, the cannula includes a first passageway for the passage of aerosol precursor composition, and a second passage way for passage of air into the container.

In some example implementations of the atomizer of any preceding or any subsequent example implementation, or any combination thereof, a second cannula that is also engaged with the septum when the container and the atomizer are coupled, the second cannula and the septum being engaged to enable passage of air into the container.

In some example implementations of the atomizer of any preceding or any subsequent example implementation, or any combination thereof, a porous element in the reservoir and configured to be at least partially saturated with the aerosol precursor composition in the reservoir.

In some example implementations of the atomizer of any preceding or any subsequent example implementation, or any combination thereof, a transport component to enable communication of aerosol precursor composition from the porous element to the heating element.

In some example implementations of the atomizer of any preceding or any subsequent example implementation, or any combination thereof, the connector is configured to threadably couple the atomizer with the container.

In some example implementations of the atomizer of any preceding or any subsequent example implementation, or any combination thereof, the connector is configured to snap fit the container and the atomizer.

In some example implementations of the atomizer of any preceding or any subsequent example implementation, or any combination thereof, the connector is configured to pressure fit the container and the atomizer.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Aerosol delivery devices are often configured in a manner that mimics aspects of certain traditional smoking devices such as cigarettes or cigars. In this regard, aerosol delivery devices typically define a substantially cylindrical configuration. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. Aerosol delivery devices often include a control body and a cartridge which attach in an end-to-end relationship to define the substantially cylindrical configuration.

While such configurations may provide a look and feel that is similar to traditional smoking articles, these configurations may suffer from certain detriments. For example, cylindrically-configured aerosol delivery devices may not define attachment points usable to retain the aerosol delivery device in a desired position when not in use. Further, the cylindrical configuration may result in the mouthpiece being exposed to the surrounding environment and therefore susceptible to contamination. Accordingly, it may be desirable to provide aerosol delivery devices in configurations that differ from shapes associated with traditional smoking articles.

In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or capacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

In various examples, an aerosol delivery device can comprise a reservoir configured to retain the aerosol precursor composition. The reservoir may be a void space for bulk fluid or particularly can be formed of a porous material (e.g., a rigid, porous material or primarily fibrous material) and thus may be referred to as a porous substrate.

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. In further example implementations, organic cotton, polyethylene terephthalate, porous ceramic or glass, or porous sintered can be used. A reservoir may be substantially in the form of a container and may include a fibrous material included therein. In other implementations, the reservoir may be formed of a glass, plastic, or other materials not explicitly set forth herein.

In some implementations, the aerosol delivery device can include an indicator, which may comprise one or more light emitting diodes or a graphical user interface via a display. The indicator can be in communication with the control component through a connector circuit and illuminate, for example, during a user draw on the mouthend as detected by the flow sensor.

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

Figure 1A:
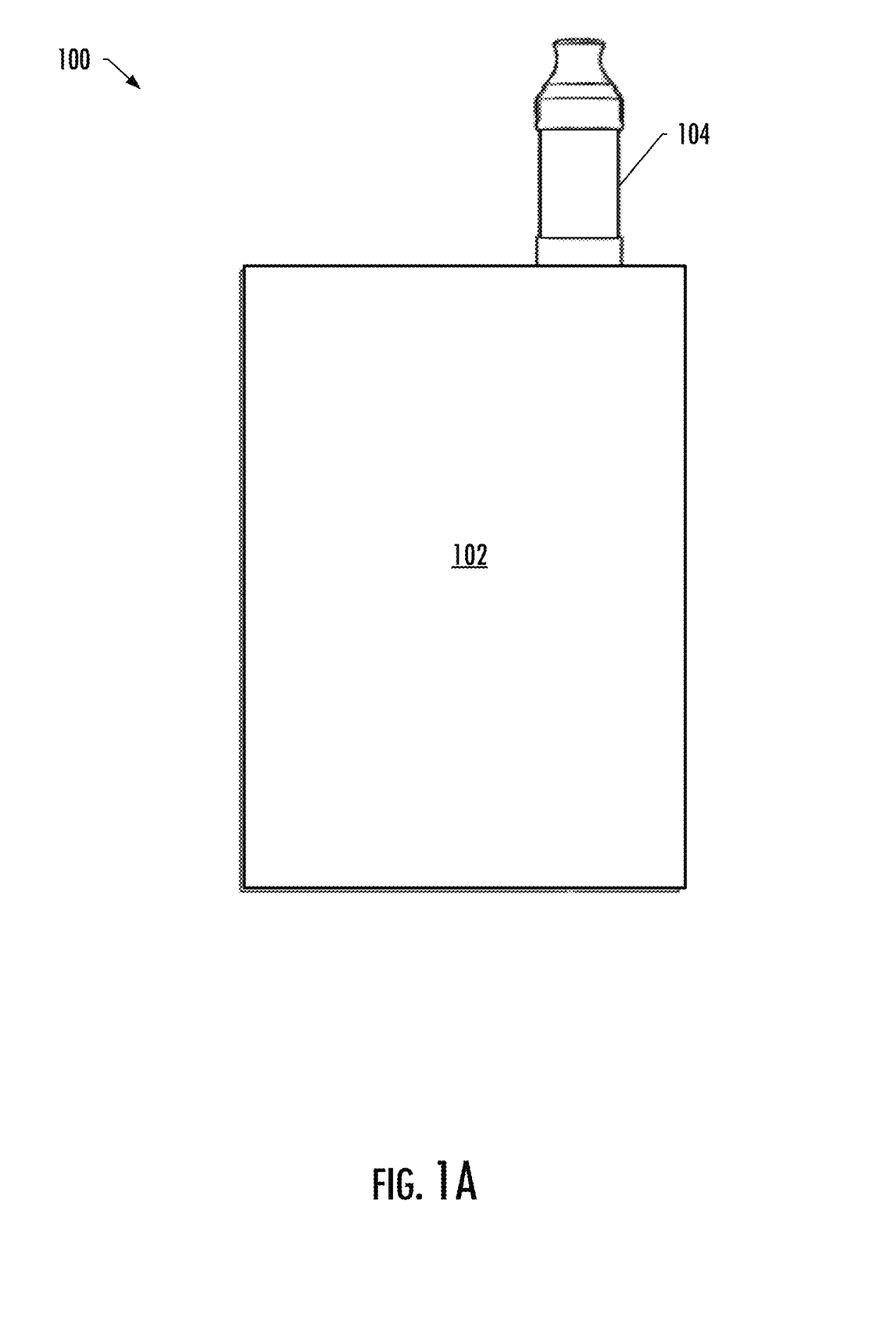
FIG. 1A illustrates a front view of an aerosol delivery device including a cartridge coupled to a control body, according to an example implementation of the present disclosure.
Figure 1B:
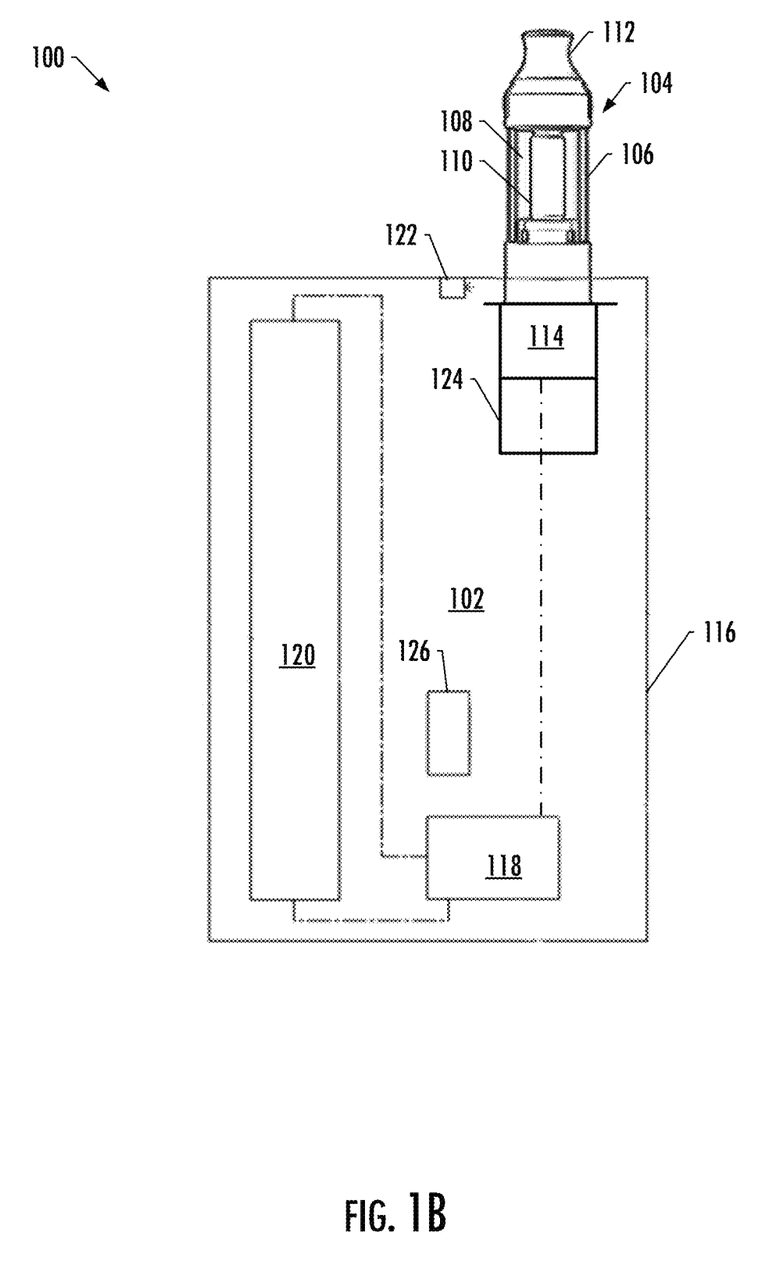
FIG. 1B illustrates a sectional view of the aerosol delivery device of FIG. 1A, according to an example implementation of the present disclosure.

FIG. 1A illustrates a front view of an aerosol delivery device 100, and FIG. 1B illustrates a modified sectional view through the aerosol delivery device (collectively FIG. 1), according to an example implementation of the present disclosure. As illustrated, the aerosol delivery device may include a control body 102 and a cartridge 104. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. In some examples, the aerosol delivery device may be substantially rod-like, substantially tubular shaped, or substantially cylindrically shaped in some example implementations when the cartridge and the control body are in an assembled configuration. In other examples, further shapes and dimensions are encompassed—e.g., a rectangular or triangular cross-section, multifaceted shapes, or the like. The cartridge and control body may include separate, respective housings or outer bodies, which may be formed of any of a number of different materials. The housing may be formed of any combination of suitable, structurally-sound materials. In some examples, the housing may be formed of at least one of a metal or alloy, such as stainless steel, aluminum or the like. Other suitable materials include various plastics (e.g., polycarbonate), metal-plating over plastic, glass, and the like.

In some example implementations, one or both of the control body 102 or the cartridge 104 of the aerosol delivery device 100 may be referred to as being disposable or as being reusable. The aerosol delivery device may include various other components disposed within the control body or cartridge or otherwise coupled thereto. These components may be distributed between the control body and the cartridge in any of various manners. For example, the control body may have a replaceable battery or removable battery or a rechargeable battery and thus may be combined with any type of recharging technology, including connection to a typical alternating current electrical outlet, connection to a car charger (i.e., a cigarette lighter receptacle), connection to a computer, such as through a universal serial bus (USB) cable or connector, or connection to a photovoltaic cell (sometimes referred to as a solar cell) or solar panel of solar cells. For example, an adaptor including a USB connector at one end and a control body connector at an opposing end is disclosed in U.S. Pat. Pub. No. 2014/0261495 to Novak et al., which is incorporated herein by reference in its entirety.

In one example implementation, the control body 102 and cartridge 104 forming the aerosol delivery device 100 may be removably coupled to one another. Examples of aerosol delivery devices that may be configured to be disposable and/or which may include first and second outer bodies that are configured for permanent coupling are disclosed in U.S. Pat. App. No. 2015/0216232 to Bless et al., which is incorporated herein by reference in its entirety. In another example implementation, the cartridge and control body may incorporate the components, aspects, and features disclosed herein. However, in another example implementation, the control body and cartridge may be configured to be separable such that, for example, the cartridge may be refilled or replaced.

FIG. 1B illustrates a more particular example of the aerosol delivery device 100 in which the components are representative of the components that may be present in a suitable control body 102 and a cartridge 104 and are not intended to limit the scope of control body and cartridge components that are encompassed by the present disclosure.

The cartridge 104 can be formed of an atomizer 106 enclosing a reservoir 108 configured to retain the aerosol precursor composition, and including a heater 110 (sometimes referred to as a heating element). In various configurations, this structure may be referred to as a tank; and accordingly, the terms "cartridge," "tank" and the like may be used interchangeably to refer to a shell or other housing enclosing a reservoir for aerosol precursor composition, and including a heater.

In some examples, the reservoir 108 of the cartridge 104 may comprise a refillable reservoir. The reservoir may be configured to retain the aerosol precursor composition. In some example implementations, the reservoir particularly can be formed of a porous material (e.g., a fibrous material) and thus may be referred to as a porous substrate (e.g., a fibrous substrate). A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein. In other implementations, the reservoir may be formed of a glass, ceramic, plastic, or other materials not explicitly set forth herein.

The reservoir 108 may be in fluid communication with a liquid transport element adapted to wick or otherwise transport an aerosol precursor composition stored in the reservoir housing to the heater 110. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 110. The heater in these examples may be resistive heating element such as a coil. Example materials from which the coil may be formed include Titanium (Ti), Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). The heating element may comprise a wire structure defining a mesh, screen or lattice structure positioned about the liquid transport element.

Example materials from which the wire mesh, screen, or lattice that may be formed of, or include titanium, platinum, silver, palladium, Kanthal (FeCrAl), Nichrome, Molybdenum disilicide (MoSi$_2$), molybdenum silicide (MoSi), Molybdenum disilicide doped with Aluminum (Mo(Si,Al)$_2$), graphite and graphite-based materials; and ceramic (e.g., a positive or negative temperature coefficient ceramic). Example implementations of heaters or heating members useful in aerosol delivery devices according to the present disclosure are further described below, and can be incorporated into devices described herein.

A mouthpiece 112 having an opening defined therein may be coupled to the atomizer 106 (e.g., at the mouth end) to allow for egress of formed aerosol from the cartridge 104.

The cartridge 104 may also include one or more electronic components, which may include an integrated circuit, a memory component, a sensor, or the like. The electronic components may be adapted to communicate with a control component of the control body and/or with an external device by wired or wireless means. The electronic components may be positioned anywhere within the cartridge or a base 114 thereof.

As illustrated in FIG. 1B, the control body 102 can be formed of a control body shell 116 that can include a control component 118 (e.g., a printed circuit board (PCB), an integrated circuit, a memory component, a microprocessor, individually or as part of a microcontroller, and the like), a power source 120, and one or more indicators 122 such as light-emitting diodes (LEDs), and such components can be variably aligned. The power source may include, for example, a battery (single-use or rechargeable), supercapacitor or the like. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173, 266, filed Feb. 5, 2014, to Sears et al.; which are incorporated herein by reference.

The control component 118 may be configured to direct electrical power from the power source 120 to the heater 110 to heat aerosol precursor composition retained in the cartridge 104 to produce a vapor, which may occur during a user draw on a mouthpiece 112 of the cartridge. The control component 118 may include a number of electronic components, and in some examples may be formed of an electronic or printed circuit board (PCB) that supports and electrically connects the electronic components. Examples of suitable electronic components include a microprocessor or processor core, an integrated circuit (IC), a memory, and the like.

In some examples, the control component 118 may include a microcontroller with an integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327, 776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The control body 102 and the cartridge 104 may include components adapted to facilitate a fluid engagement therebetween. As illustrated in FIG. 1B, the control body can include a connector 124. The base 114 of the cartridge can be adapted to engage the connector and can include a projection adapted to fit within the connector. Such engagement can facilitate a stable connection between the control body and the cartridge as well as establish an electrical connection between the battery 120 and control component 118 in the control body, and the heater 110 in the cartridge. Further, the control body shell 116 can include an air intake, which may be a notch in the shell where it connects to the connector that allows for passage of ambient air around the connector and into the shell where it then passes through the connector and into the cartridge through the projection.

A connector and a base useful according to the present disclosure are described in U.S. Pat. App. Pub. No. 2014/ 0261495 to Novak et al., which is incorporated herein by reference in its entirety. However, various other examples of structures, shapes and components may be employed to couple the base to the connector. In some examples the connection between the base of the cartridge 104 and the connector of the control body 102 may be releasable such that, for example, the control body may be reused with one or more additional cartridges that may be disposable and/or refillable.

The reservoir 108 illustrated in FIG. 1B can be substantially formed into the shape of a tube encircling the interior of the atomizer 106, in this example. An aerosol precursor composition can be retained in the reservoir. Liquid components, for example, can be retained by the reservoir. The reservoir can be in fluid connection with the liquid transport element. The liquid transport element can transport the aerosol precursor composition stored in the reservoir via capillary action to the heater 110 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices as described herein. In particular, specific combinations of heating members and transport elements as further described below may be incorporated into devices.

In use, when a user draws on the aerosol delivery device 100, airflow is detected by a flow sensor, and the heater 110 is activated to vaporize components of the aerosol precursor composition. In some implementations, a manual button may be used exclusively, or in combination with a flow sensor, to activate the heater. Alternatively, the manual button may be depressed to activate the heater in lieu of a flow sensor. Drawing upon the mouthpiece 112 of the aerosol delivery device causes ambient air to enter the air intake and pass through the connector 124 and a central opening in a projection of the base 114. In the cartridge 104, the drawn air combines with the formed vapor to form an aerosol. The aerosol is whisked, aspirated or otherwise drawn away from the heater and out the opening in the mouthpiece of the aerosol delivery device.

An input element 126 may be included with the aerosol delivery device 100. The input element may be included to allow a user to control functions of the device and/or for output of information to a user. For example, a user may utilize the input element to vaporize an aerosol precursor composition and/or activate an on/off function. The input element may comprise a pushbutton or other switch configured to receive an input from a user. When the input element is actuated, the aerosol delivery device may produce an output corresponding to a status of the aerosol delivery device. For example, the aerosol delivery device may output sound, vibration, or light. Any component or combination of components may be utilized as an input for controlling the function of the device. For example, one or more pushbuttons may be used as described in U.S. patent application Ser. No. 14/193,961, filed Feb. 28, 2014, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some example implementations, a computing device such as a mobile computer (e.g., smartphone, tablet computer) may be used as an input element in addition to or in lieu of an input element 126 on the aerosol delivery device itself. In particular, the aerosol delivery device 100 may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such implementations, application software may be used in connection with the computing device to input control instructions to the aerosol delivery device, such control instructions including, for example, the ability to form an aerosol of specific composition by choosing the nicotine content and/or content of further flavors to be included.

In some examples, the aerosol delivery device 100 may include a number of additional hardware-implemented or software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 118 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 120 may vary over the course of each puff on the device 100 according to a power control mechanism. The device may include a "long puff" safety timer such that in the event that a user or an inadvertent mechanism causes the device to attempt to puff continuously, the control component 118 may control at least one functional element to terminate the puff automatically after some period of time (e.g., four seconds). Further, the time between puffs on the device may be restricted to greater than a period of time (e.g., one hundred (100) milliseconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor, such as by permanently disabling the aerosol delivery device in order to prevent inadvertent heating. A puffing limit switch may deactivate the device in the event of a pressure sensor fail causing the device to continuously activate without stopping after the four second maximum puff time.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device 100 most preferably incorporates the control component 118 or another control mechanism for controlling the amount of electric power to the heater 110 during draw. In some implementations, the control component may effect control of different power settings on the aerosol delivery device. For example, at least a low, medium, and high power setting may be controlled for adjusting aerosol production within the aerosol delivery device. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

The aerosol delivery device 100 can also incorporate the flow sensor or another sensor or detector for control of supply of electric power to the heater 110 when aerosol generation is desired (e.g., upon draw during use). As such, for example, there is provided a manner or method of turning off the power supply to the heating element when the aerosol delivery device is not be drawn upon during use, and for turning on the power supply to actuate or trigger the generation of heat by the heating element during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.'

Representative types of aerosol precursor components and formulations also are set forth and characterized in U.S. Pat. No. 7,217,320 to Robinson et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 5 g, generally less than about 2.5 g, often less than about 2 g and frequently less than about 1 g.

Additional representative types of components that yield visual cues or indicators may be employed in the aerosol delivery device 100, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

Figure 2:
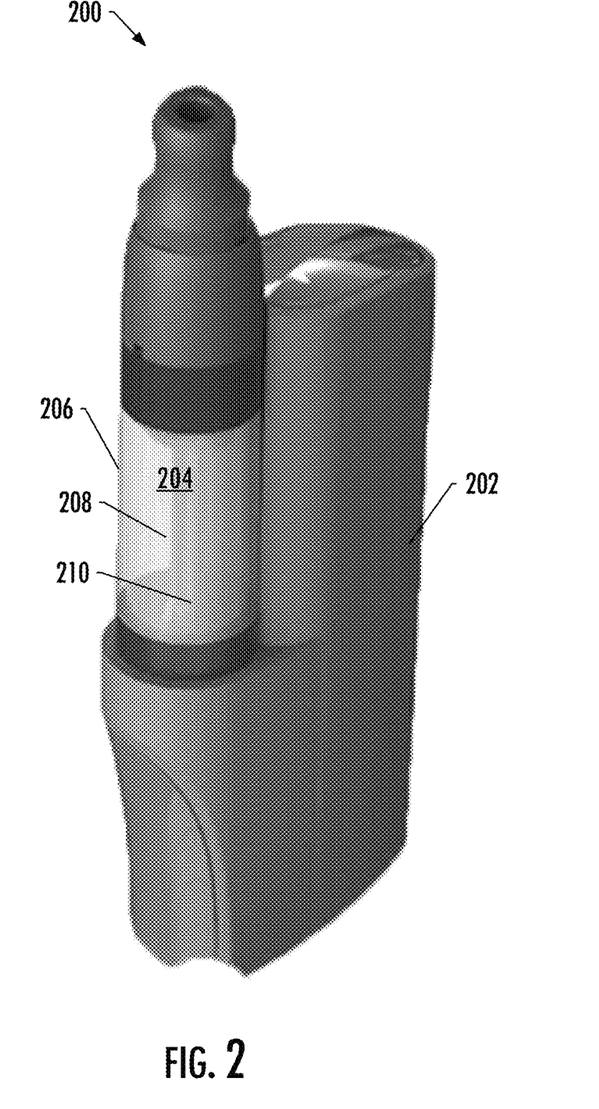
FIG. 2 is a perspective view of an aerosol delivery device according to an example implementation of the present disclosure.

FIG. 2 illustrates a perspective view of a suitable aerosol delivery device 200 that in some examples may correspond to the aerosol delivery device 100 of FIG. 1. As shown, the aerosol delivery device can comprise a control body 202 and a cartridge 204, which may correspond to respectively the control body 102 and cartridge 104 of FIG. 1. The control body may define an ergonomic shape configured to comfortably fit within a user's hand. The shape of the housing, however, is not limited and may be any shape that accommodates the various elements as described herein. In some implementations, the housing may be expressly non-cylindrical.

As previously explained, the cartridge 204 can be formed of an atomizer 206 enclosing a reservoir 208 therein, which in some examples may correspond to the atomizer 106 and reservoir 108 of FIG. 1. In some example implementations, the reservoir may be a refillable reservoir, and a container of aerosol precursor composition may be provided for refilling the reservoir. The cartridge and container may be removably, sealably connectable to one another such that the sealed coupling between the cartridge and the container may be configured to enable the transfer of aerosol precursor composition between the container and the aerosol delivery device.

Figure 3:
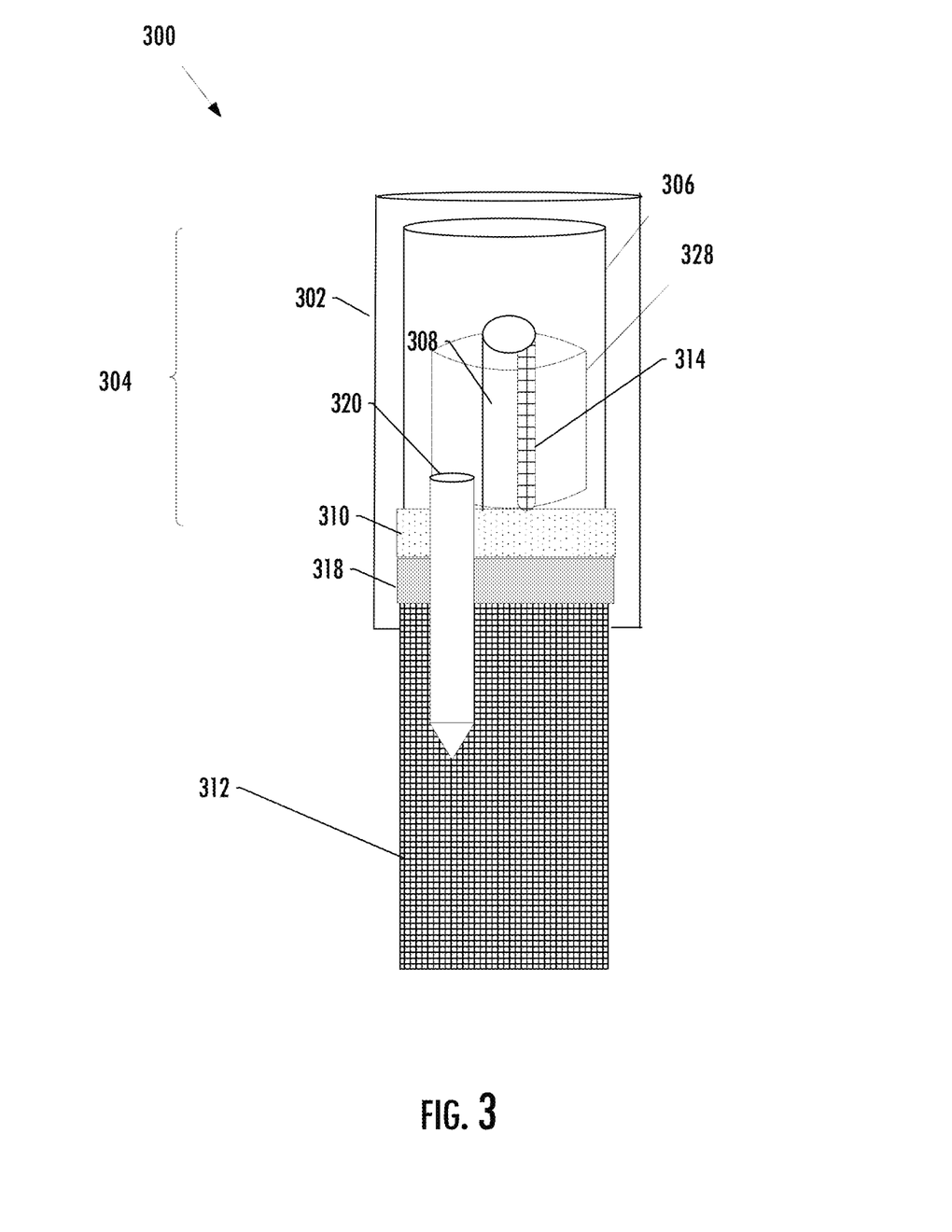
FIGS. 3-3B illustrates a partially cut-away view of the cartridge of FIG. 2, according to an example implementations of the present disclosure.

FIG. 3 illustrates a portion of a cartridge 300 of an aerosol delivery device that in some examples may correspond to the cartridge 204 of FIG. 2, or the cartridge 104 of FIGS. 1A, 1B. As shown, the cartridge may include an atomizer 304 with an outer wall 302, reservoir 306, and heater 308 that may correspond to respective ones of the atomizer 206, reservoir 208, and heater 210 of the cartridge 204 of FIG. 2.

As more particularly shown in FIG. 3, the cartridge 300 may comprise a container 312 of aerosol precursor composition, and the atomizer 304 enclosing the reservoir 306 configured to receive and carry aerosol precursor composition. In some example implementations, the reservoir is a refillable reservoir, and the container of aerosol precursor composition is provided for refilling the reservoir. The container and the atomizer are removably coupleable with one another via a connector 310.

As shown in FIG. 3, the container 312 may include a septum 318, and the atomizer 304 may include the connector 310 including a cannula 320 that are engaged when the container and the atomizer are coupled to enable passage of aerosol precursor composition from the container to the reservoir 306. The septum may provide a sealed coupling between the cannula and the container to enable the transfer of aerosol precursor composition between the container and the reservoir and to prevent leakage.

The container 312 may include a cylindrical portion defining a large aperture adjacent to a cavity but which may closed off by the septum 318 where the septum may be solid material. In some implementations, the septum may be molded or otherwise formed from any suitable elastomeric material such as silicone, rubber or the like. Also, in some implementations, the septum may be comprised of a metallic foil material. Further, in some implementations, the septum may be made of different elastomeric materials, which may have different rigidity and flexibility. For example, the septum may have a weakened core of the same or different elastomeric material from the rest of the septum to facilitate movement of the cannula through the septum. At the same time, the integrity of the septum is maintained because the rest is formed of strong elastomeric material.

The cannula 320 may be inserted through the material of the septum 318 to bring a distal opening of the cannula into communication with aerosol precursor composition within the container 312 to facilitate fluid flow through the lumen of the cannula. In some implementations, the cannula may include a sharp distal end to penetrate a rigid septum and a blunt end to penetrate a septum that is less rigid. The septum may self-seal around the cannula when penetrated by the cannula. The cannula may be contained within an outer wall 302 of the atomizer 304 to shroud the cannula and reduce the risk of injuries from touching the sharp distal of the cannula when the cannula is removed from the container. As illustrated in FIG. 3, the outer wall may fit over a cylindrical portion of the container as the cannula extends into and through the septum into the cavity.

In some examples, the atomizer 304 may include a heating element 308 controllable to activate and vaporize components of the aerosol precursor composition in the reservoir 306. In this regard, the heating element may include a resistive heating element in the form of a metal wire coil. The resistive heating element may include positive and negative terminals at the opposing ends thereof for facilitating current flow through the resistive heating element and for attachment of the appropriate wiring (not illustrated) to form an electrical connection of the resistive heating element with the power source 212 when the atomizer 304 is connected to the control body 202. When the atomizer is connected to the control body, an electrical connection may form such that current controllably flows from the power source to the resistive heating element.

Figure 3A:
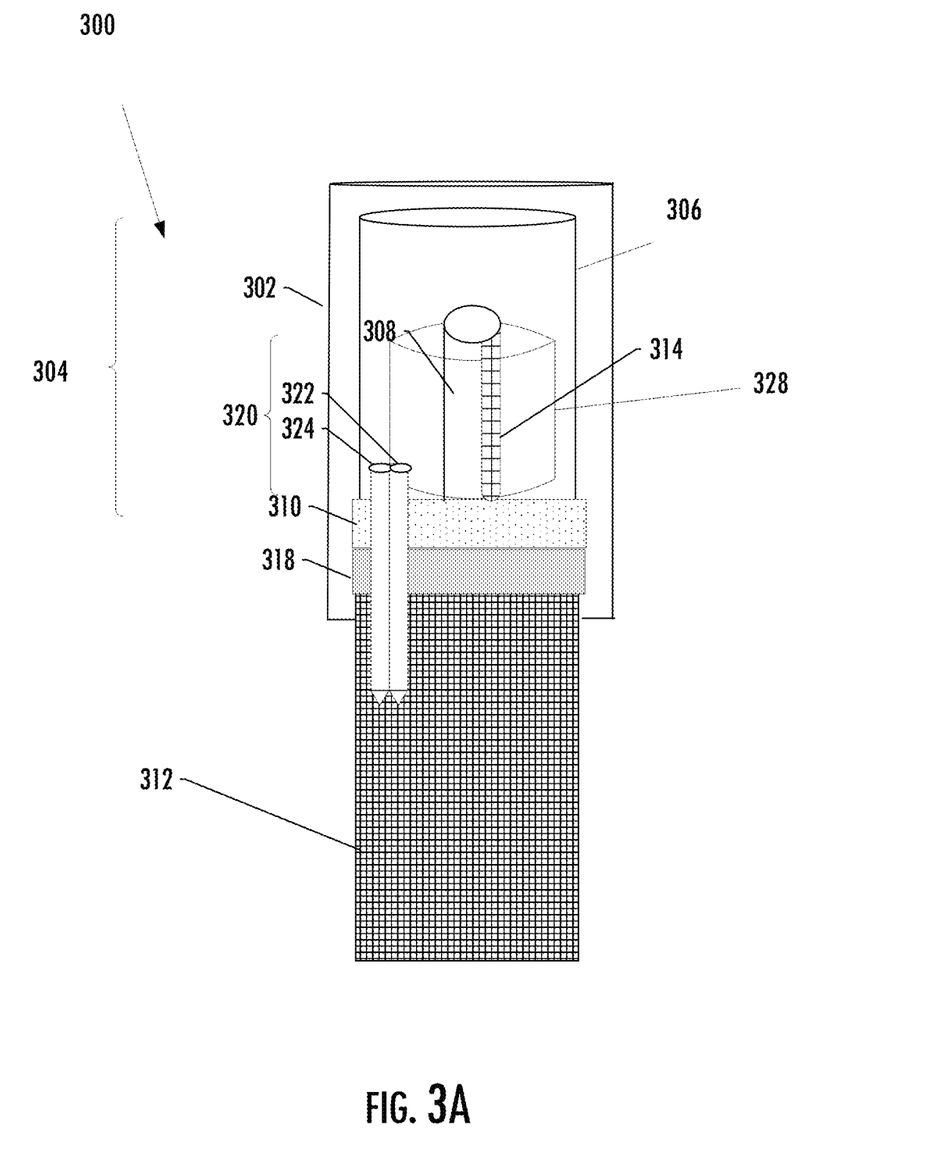
Figure 3B:
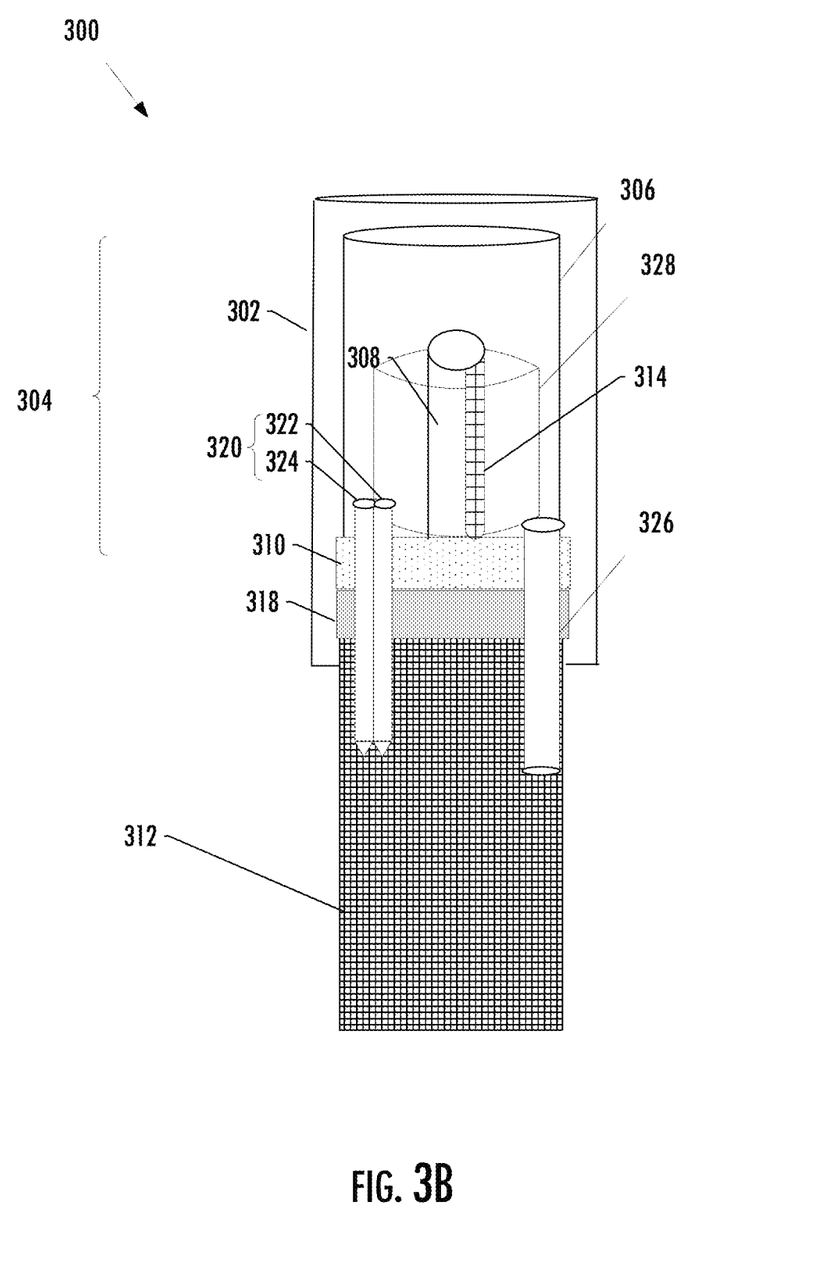

As illustrated in FIG. 3A, in some examples, the cannula 320 may include a first passageway 322 for the passage of aerosol precursor composition, and a second passageway 324 for passage of air into the container. As illustrated in FIG. 3 the first passageway is configured to provide a capillary passageway and control flow of aerosol precursor composition from the container 312 to the heating element 308 in the reservoir 306. The second passageway may be included to allow replacement air into the container 312 as the precursor composition level subsides. In an alternative implementation, as shown in FIG. 3B the atomizer 304 may further include a second cannula 326 that is also engaged with the septum 318 when the container 312 and the atomizer are coupled, the second cannula and the septum being engaged to enable passage of air into the container.

In some implementations, the atomizer 304 may further comprise a porous element 328 in the reservoir 306 and configured to be at least partially saturated with the aerosol precursor composition in the reservoir, as illustrated in FIG. 3. In particular, the porous element may be configured to receive aerosol precursor composition from the first passageway 322 of the cannula 320. In some implementations, the porous element may comprise nickel, stainless steel fiber felt, macromolecular polymer foam or foamed ceramics, or any material with suitable capabilities in liquid absorption and diffusion, and the ability to absorb the precursor composition in the reservoir.

In some implementations, the atomizer 304 may further comprise a transport component 314 to enable fluid communication of aerosol precursor composition from the porous element 322 to the heating element 308. As mentioned above, the reservoir 306 may be in fluid communication with the transport element 314 adapted to wick or otherwise transport aerosol precursor composition stored in the reservoir to the heater 308. A transport element for use according to the present invention can be any component that functions to transport one or more components of an aerosol precursor composition from a reservoir to an aerosolization zone in the smoking article where a resistive heating element aerosolizes the aerosol precursor composition and thus form an aerosol. In particular, the transport element particularly may be a wick that utilizes capillary action in the transport of aerosol precursor composition. A wick for use according to the implementations herein may be any material that provides sufficient wicking action to transport one or more components of the aerosol precursor composition to an aerosolization zone. Non-limiting examples include natural and synthetic fibers, such as cotton, cellulose, polyesters, polyamides, polylactic acids, glass fibers, combinations thereof, and the like. Other exemplary materials that can be used in wicks include metals, ceramics, and carbonized materials (e.g., a foam or monolith formed of a carbonaceous material that has undergone calcining to drive off non-carbon components of the material). The term "wick" is also intended to encompass capillary tubes, and any combination of elements providing the desired capillary action can be used.

In some implementations, the container 312 and the atomizer 304 are threadably coupleable with one another. Particularly, the atomizer may be internally threaded where the container may include an externally threaded portion. The container may be sealably connectable with the atomizer by being threadable onto the internally threaded portion of the atomizer.

In some implementations, the container 312 and the atomizer 304 are engagable in a snap fit connection with one another. In particular, a snap fit engagement may be provided for releasably joining the container and atomizer and enable a secure connection. One example of a snap fit connection includes a locking arm integrally formed on the atomizer and a rigid locking frame integrally formed on the container (not shown). The locking arm may include a projection which may define a step portion and a cam surface. The locking frame may generally have rectangular shape and may define a generally rectangular aperture adapted to receive the locking arm. An integral resilient tab may extend outwardly from the atomizer and into the locking frame aperture. The resilient tab may be deflected by insertion of the locking arm into the locking frame aperture and may maintain a secure engagement between the locking arm and locking frame.

In some implementations, the container 312 and the atomizer 304 are engagable in a pressure fit connection with one another. One example of a pressure fit connection includes recessed receptacles formed the container (not shown). These receptacles may receive pins (not shown) that project from the atomizer. The engagement between the container and the atomizer may be in the manner of a press-fit engagement. Alternatively, an interior lip (not shown) may be provided along the container and this lip may be received in a corresponding recess of the atomizer.

In some examples, a control component may be configured to control operation of functional element(s) of the aerosol delivery device based on the engagement of the container 312 and atomizer 304. As described in the examples below, this control component may be the control component 208 of the control body 102. It should be understood, however, that the control component may be instead another control component of the control body or the atomizer 104.

Functional element(s) of the aerosol delivery device 100 may be controlled in any of a number of different manners in based on the on the engagement of the container 312 and atomizer 304. For example, functional element(s) may be controlled to alter a locked state of the aerosol delivery device. This may include, for example, enabling or disabling one or more components of the aerosol delivery device for operation when the container and atomizer are engaged In addition to or in lieu of control to alter a locked state of the aerosol delivery device 100, an indicator 122 (e.g., visual indicator, audio indicator, haptic indicator) may be controlled to provide a user-perceptible feedback (e.g., visual, audible, haptic feedback) that indicates the amount of aerosol precursor composition. The feedback may include, for example, a visual, audible and/or haptic notification that the container 312 and atomizer 306 are engaged or not engaged. In instances in which container and atomizer not engaged, the indicator may provide the user-perceptible feedback such as an alarm, buzzer, vibration or visual indicator (e.g., LED) to warn the user.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-3 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
   a container of aerosol precursor composition; and
   an atomizer enclosing a reservoir configured to receive and carry the aerosol precursor composition, the atomizer being controllable to activate and vaporize components of the aerosol precursor composition in the reservoir;
   wherein the container and the atomizer are removably coupleable with one another via a connector of the atomizer, wherein the container includes a septum and the connecter includes a cannula, and wherein the cannula and the septum are engaged when the container and the atomizer are coupled to enable passage of the aerosol precursor composition from the container to the reservoir through the cannula, and wherein the cannula includes a first opening within the reservoir and a second opening within the container when the cannula and the septum are engaged, and wherein the cannula includes a first enclosed passageway for the passage of the aerosol precursor composition and a second enclosed passageway for passage of air into the container; and
   wherein the atomizer further includes a second cannula that is also engaged with the septum when the container and the atomizer are coupled, the second cannula and the septum being engaged to further enable passage of air into the container.

2. The aerosol delivery device of claim 1, wherein the atomizer further comprises a porous element in the reservoir and configured to be at least partially saturated with the aerosol precursor composition in the reservoir.

3. The aerosol delivery device of claim 2, wherein the atomizer further comprises a transport component to enable fluid communication of the aerosol precursor composition from the porous element to the atomizer.

4. The aerosol delivery device of claim 1, wherein the container and the atomizer are threadably coupleable with one another.

5. The aerosol delivery device of claim 1, wherein the container and the atomizer are engageable in a snap fit or pressure fit connection with one another.

6. A container of aerosol precursor composition, the container comprising:
   a connector configured to removably couple the container with an atomizer enclosing a reservoir configured to receive and carry the aerosol precursor composition, the atomizer being controllable to activate and vaporize components of the aerosol precursor composition in the reservoir; and
   a septum that is engaged with a cannula of the connector when the container and the atomizer are coupled to enable passage of the aerosol precursor composition from the container to the reservoir of the atomizer through the cannula, wherein the cannula includes a first opening within the reservoir and a second opening within the container when the cannula and the septum are engaged, and wherein the cannula includes a first enclosed passageway for the passage of the aerosol precursor composition and a second enclosed passageway for passage of air into the container, wherein the septum is further engaged with a second cannula of the atomizer when the container and the atomizer are coupled, the septum and the second cannula being engaged to further enable passage of air into the container.

7. The container of claim 6, wherein the septum is engaged with the cannula to enable passage of the aerosol precursor composition from the container to a porous element in the reservoir and configured to be at least partially saturated with the aerosol precursor composition in the reservoir.

8. The container of claim 6, wherein the connector is configured to threadably couple the container with the atomizer.

9. The container of claim 6, wherein the connector is configured to snap fit or pressure fit the container with the atomizer.

10. An atomizer for an aerosol delivery device, the atomizer comprising:
   a connector configured to removably couple the atomizer with a container of aerosol precursor composition;
   a reservoir configured to receive and carry the aerosol precursor composition;
   a cannula of the connector that is engaged with a septum of the container when the atomizer and the container are coupled to enable passage of the aerosol precursor composition from the container to the reservoir through the cannula, and wherein the cannula includes a first opening within the reservoir and a second opening within the container when the cannula and the septum are engaged, and wherein the cannula includes a first enclosed passageway for the passage of the aerosol precursor composition and a second enclosed passageway for passage of air into the container; and
   a second cannula that is also engaged with the septum when the container and the atomizer are coupled, the second cannula and the septum being engaged to further enable passage of air into the container,
   wherein the atomizer is controllable to activate and vaporize components of the aerosol precursor composition in the reservoir.

11. The atomizer of claim 10, further comprising a porous element in the reservoir and configured to be at least partially saturated with the aerosol precursor composition in the reservoir.

12. The atomizer of claim 11 further comprising a transport component to enable communication of the aerosol precursor composition from the porous element to the atomizer.

13. The atomizer of claim 10, wherein the connector is configured to threadably couple the atomizer with the container.

14. The atomizer of claim 10, wherein the connector is configured to snap fit or pressure fit the container and the atomizer.

* * * * *